| United States Patent [19] | [11] 3,931,213 |
|---|---|
| Kaminski et al. | [45] Jan. 6, 1976 |

[54] 3-CHLORO-2-OXAZOLIDINONES

[75] Inventors: James J. Kaminski; Nicolae S. Bodor, both of Lawrence, Kans.

[73] Assignee: Interx Research Corporation, Lawrence, Kans.

[22] Filed: Dec. 18, 1974

[21] Appl. No.: 533,945

[52] U.S. Cl............................. 260/307 C; 424/272
[51] Int. Cl.² ...................................... C07D 263/22
[58] Field of Search ............................... 260/307 C

[56] References Cited
UNITED STATES PATENTS 3,591,601   7/1971   Walles ................................ 260/307
3,850,920   11/1974  Walles ........................... 260/247.7 J

*Primary Examiner*—Raymond V. Rush
*Attorney, Agent, or Firm*—Charles N. Blitzer

[57] ABSTRACT

Antibacterially effective 3-chloro-2-oxazolidinones are prepared by chlorination of an appropriate 2-oxazolidinone either with elemental chlorine in an aqueous medium or with a mono-, di- or tri-chloroisocyanuric acid (cyanuric chloride) in an inert organic solvent. The 2-oxazolidinones are, in turn, prepared by reaction of an appropriate ethanolamine either with a di-lower-alkyl carbonate in the presence of a strong base or with urea at an elevated temperature.

7 Claims, 2 Drawing Figures

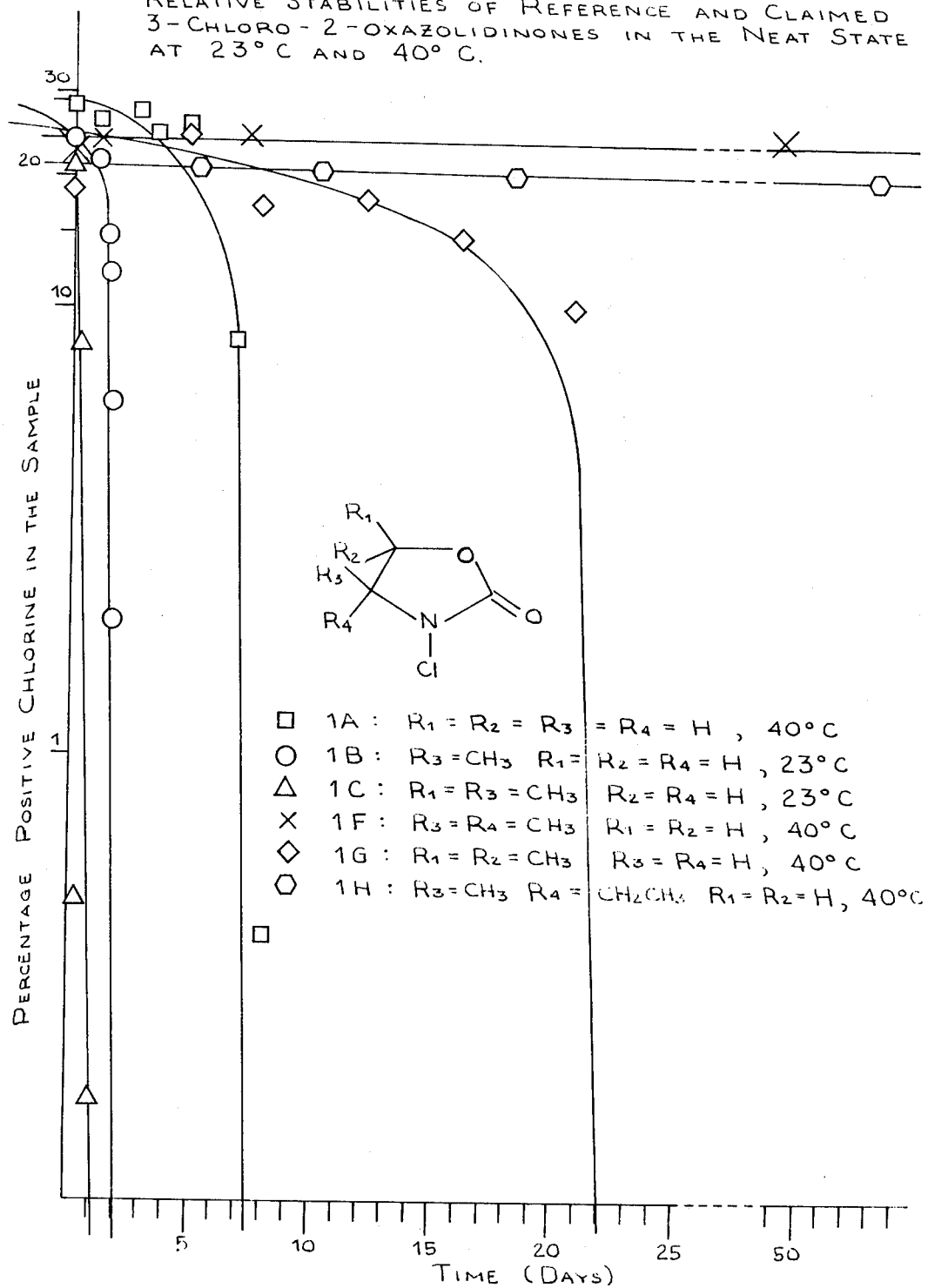

3-CHLORO-2-OXAZOLIDINONES

BACKGROUND OF THE INVENTION

A. Field of the Invention

This invention relates to 3-chloro-2-oxazolidinones useful in the art of chemistry and having antibacterial activity.

B. Description of the Prior Art

Walles U.S. Pat. No. 3,591,601 (patented July 6, 1971) discloses certain 3-halo-2-oxazolidinones having the formula:

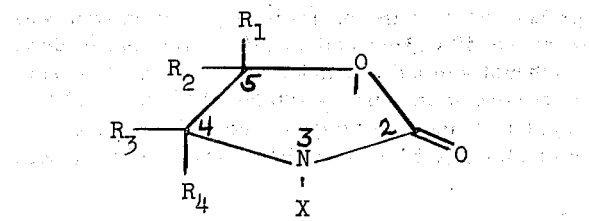

where X is broadly defined as bromine or chlorine, and $R_1$, $R_2$, $R_3$ and $R_4$ are broadly defined, inter alia, as hydrogen or lower-alkyl containing from one to four carbon atoms. The compounds are said to be useful "in germicidal, bleaching, and chemical reaction applications."

While the above definitions are broadly embracive of compounds having a quaternary carbon at the 4- and-/or 5-positions of the oxazolidinone ring, i.e., compounds where either each of $R_1$, $R_2$, $R_3$ and $R_4$ is lower-alkyl or compounds where each of $R_1$ and $R_2$ or each of $R_3$ and $R_4$ is lower-alkyl (the other pair being hydrogen), such compounds are not specifically taught by Walles, who discloses only compounds where the 4- and 5-carbon atoms are either unsubstituted or where either one or both of the 4- and 5-carbon atoms bear a single lower-alkyl group. Thus, of the 2-oxazolidinones having the above general structure where each of $R_1$, $R_2$, $R_3$ and $R_4$ are either hydrogen or lower-alkyl, Walles discloses only the following species. (The "Walles Cpd. Nos." are adopted here for reference purposes hereinafter.)

| Walles Cpd. No. | $R_1$ | $R_2$ | $R_3$ | $R_4$ | X |
|---|---|---|---|---|---|
| 1 | $CH_3$ | H | H | H | Cl |
| 2 | $C_2H_5$ | H | H | H | Cl |
| 3 | H | H | H | H | Cl |
| 4 | $CH_3$ | H | H | H | Br |
| 5 | $CH_3$ | H | $CH_3$ | H | Cl |
| 6 | $C_4H_9$ | H | H | H | Br |

Certain of the above-listed Walles compounds have been prepared and it has been found that they are somewhat unstable and consequently have limited usefulness as germicidal agents. On the other hand, it has been surprisingly found that certain compounds within the ambit of the very broad disclosure of the patentee, but not specifically contemplated thereby, are surprisingly stable, in contrast with the compounds actually prepared by Walles, and possess unexpected advantageous properties as germicides.

SUMMARY OF THE INVENTION

Thus, in a composition of matter aspect, the present invention relates to certain 3-chloro-4,4-di-lower-alkyl-2-oxazolidinones and 3-chloro-5,5-di-lower-alkyl-2-oxazolidinones useful as germicidal agents.

The invention also relates to a method of inhibiting the growth of bacteria comprising treating bacteria with a bactericidally effective amount of the said 3-chloro-4,4-dilower-alkyl-2-oxazolidinones or 3-chloro-5,5-di-lower-alkyl-2-oxazolidinones and to germicidal compositions containing a bactericidally effective amount of the said 3-chloro-4,4-di-lower-alkyl-2-oxazolidinones and 3-chloro-5,5-di-lower-alkyl-2-oxazolidinones as the active ingredient in an aqueous medium.

In a process aspect, the invention relates to a process for preparing the 3-chloro-4,4-di-lower-alkyl-2-oxazolidinones and 3-chloro-5,5-di-lower-alkyl-2-oxazolidinones comprising reacting a 4,4-di-lower-alkyl-2-oxazolidinone or a 5,5-di-lower-alkyl-2-oxazolidinone with chlorine in an aqueous medium.

DETAILED DESCRIPTION INCLUSIVE OF THE PREFERRED EMBODIMENTS

Figure 1:
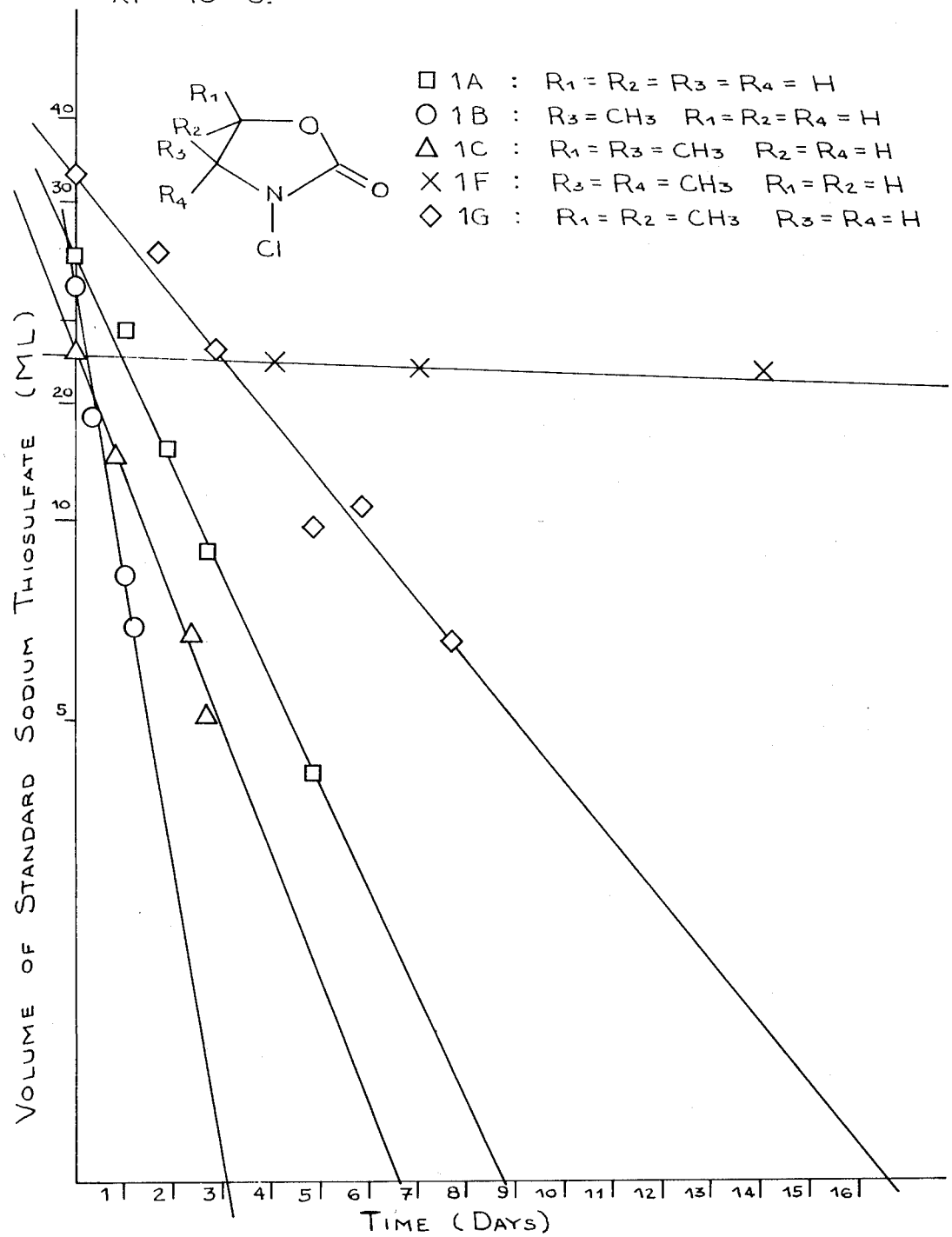

More specifically, this invention relates to 3-chloro-2-oxazolidinones having the formula:

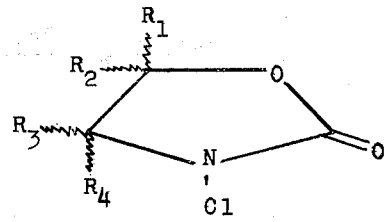

I where either $R_1$ and $R_2$ are the same or different lower-alkyl group, and $R_3$ and $R_4$ are each hydrogen or $R_1$ and $R_2$ are each hydrogen, and $R_3$ and $R_4$ are the same or different lower-alkyl group. Preferred compounds within the ambit of the invention as described above are the compounds where $R_1$ and $R_2$ are each hydrogen, and $R_3$ and $R_4$ are the same or different lower-alkyl groups, and particularly preferred compounds are those of the latter group where $R_3$ and $R_4$ are the same lower-alkyl. It will be appreciated from the foregoing that an essential feature of the compounds of the present invention is the presence of a quaternary carbon atom at either the 4- or 5-position of the 2-oxazolidinone ring.

As used herein, the term "lower-alkyl" means saturated, aliphatic hydrocarbon groups, either straight or branched-chain, containing from one to four carbon atoms, as exemplified by methyl, ethyl, propyl, isopropyl, butyl or isobutyl.

The compounds of formula I are prepared by chlorination with chlorine of the corresponding unhalogenated 4,4-di-lower-alkyl-2-oxazolidinone or 5,5-di-lower-alkyl-2-oxazolidinone having the formula:

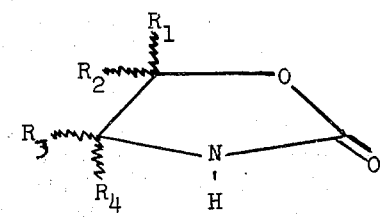

II where $R_1$, $R_2$, $R_3$ and $R_4$ have the meanings given above. The reaction is carried out in an aqueous medium and preferably at a temperature in the range from 0° to 10°C. Although higher reaction temperatures can be used, no particular advantage is gained thereby, because the halogenated final products can be hydrolyzed by the solvent, and the rate of hydrolysis increases with increase in temperature.

Alternatively, the compounds of formula I are prepared by a transhalogenation process involving reaction of a 2-oxazolidinone of formula II with a mono-, di- or trihalogenated isocyanuric acid, for example trichloroisocyanuric acid (cyanuric chloride) in an inert organic solvent, for example chloroform, methylene chloride or ethylene chloride. Reaction usually takes place at ambient temperature.

The unhalogenated 2-oxazolidinones of formula II are, in turn, prepared by reaction of an alkanolamine of formula III with a di-lower-alkyl carbonate in the presence of a strong base, for example an alkali metal lower-alkoxide, as represented by the reaction:

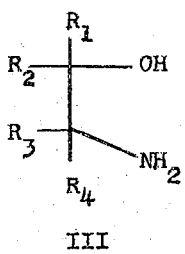 + CO(OAlkyl)$_2$ $\xrightarrow{\text{Base}}$ 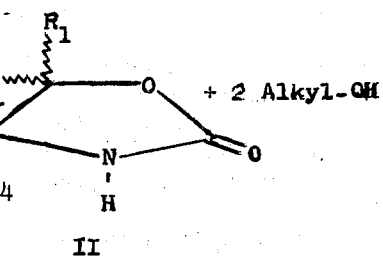 + 2 Alkyl-OH

III                         II where $R_1$, $R_2$, $R_3$ and $R_4$ have the meanings given above. The reaction is carried out by heating the reactants above the boiling point of the lower-alkanol produced in the reaction, which is distilled off as it forms.

Alternatively, the compounds of formula II are prepared by reacting an alkanolamine of formula III with urea at an elevated temperature, i.e., a temperature in the range from 150°-250°C., as represented by the reaction:

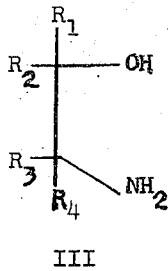 + CO(NH$_2$)$_2$ $\longrightarrow$ 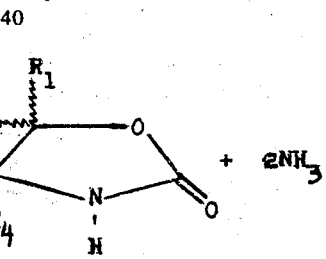 + 2NH$_3$

III where $R_1$, $R_2$, $R_3$ and $R_4$ have the meanings given above.

The alkanolamines of formula III are a generally known class of compounds.

The compounds of formula I have been tested in a standard biological test procedure, the germicidal efficiency test to be described hereinbelow, and found to possess bactericidal activity when tested against *Staphylococcus aureus* ATCC 6538. The compounds are thus useful as bactericidal agents.

The compounds of the invention can be prepared for use by dissolving them in an aqueous medium, preferably buffered to pH 7.0, and applied to surfaces or areas to be disinfected by spraying, swabbing or immersion.

The molecular structures of the compounds of the invention were assigned on the basis of their method of preparation, and study of their infrared and proton magnetic resonance spectra and were confirmed by the correspondence between calculated and found values for elementary analyses for the elements.

In the following specific examples, which illustrate the preparation of the compounds of the invention as well as reference compounds prepared for purposes of comparison, all melting points are uncorrected.

PREPARATION OF THE UNHALOGENATED 2-OXAZOLIDINONES OF FORMULA II

PREPARATION 1

A. A mixture of 61.0 g. (1.0 mole) of ethanolamine and 190 ml. (1.7 moles) of diethyl carbonate was heated to distill approximately 35 ml. of diethyl carbonate in order to ensure dryness. The mixture was cooled to 50°C., and 5 ml. of 25% sodium methoxide in methanol solution was added. The mixture was heated to remove approximately 100 ml. of ethanol. On cooling, the residue was recrystallized from chloroform to give 44.8 g. (0.51 mole, 51%) of 2-oxazolidinone, m.p. 86°-88°C.; pmr (CDCl$_3$) δ2.8-4.2 (AA'BB', 4H) and 6.0 (bs, 1H) ppm. (Lit. m.p. 87°-89°C., Homeyer, U.S. Pat. No. 2,399,118).

Following a procedure similar to that described in Preparation 1, part (A) above, the following compounds of formula II were similarly prepared:

B. 4-Methyl-2-oxazolidinone, b.p. 140°-146°/5 mm; ir-3280, 2980, 1750, 1400, 1240, 1020, and 920 cm$^{-1}$; pmr (CDCl$_3$) δ6.8 (bs, 1H), 4.4 (m, 1H), 3.9 (m, 2H) and 1.3 (d, 3H, J=6Hz) ppm, [Lit. b.p. 120°-125°/2.3 mm, Johnston et al.; J. Med. Chem., 14, 345 (1971)].

C. 4,5-Dimethyl-2-oxazolidinone, b.p. 95°-100°/0.15 mm; ir-3300, 2990, 1750, 1380, 1240, 1060 and 975 cm$^{-1}$, pmr (CDCl$_3$) δ6.9 (bs, 1H), 5.2-3.2 (m, 2H) and 1.6-1.0 (m, 6H) ppm.

Anal. Calcd. for C$_5$H$_9$NO$_2$: C,52.17; H,7.89; N,12.17. Found: C,52.37; H,8.10; N,12.35.

D. 5-Methyl-2-oxazolidinone, b.p. 123°-125°C./0.6 mm.; ir-3320 (N—H) and 1740 (C=O) cm$^{-1}$; pmr (CDCl$_3$) δ6.73 (bs, 2H), 4.80 (m, 1H), 4.0-3.0 (m, 2H) and 1.43 (d, 3H) ppm.

Anal. Calcd. for C$_4$H$_7$NO$_2$: C,47.51; H,6.98; N,13.86. Found: C,47.70; H,7.11; N,13.73.

E. 5-Ethyl-2-oxazolidinone, m.p. 50.5°-52°C.; ir-3280 (NH) and 1745 (C=O) cm$^{-1}$; pmr (CDCl$_3$) δ6.7 (bs, 1H), 4.60 (m, 1H), 4.0-3.0 (m, 2H) and 1.03 (t, 3H) ppm.

Anal. Calcd. for C$_5$H$_9$NO$_2$: C,52.16; H,7.88; N,12.17. Found: C,52.29; H,7.87; N,12.25.

F. 4,4-Dimethyl-2-oxazolidinone, m.p. 49°–51°; pmr (CDCl$_3$) δ7.0 (bs, 1H), 4.03 (s, 2H), and 1.30 (s, 6H) ppm, [Lit, m.p. 55°–56°, Homeyer, U.S. Pat. No. 2,399,118].

G. 4-Ethyl-4-Methyl-2-oxazolidinone, b.p. 110°–113°/0.3 mm; ir-3300, 3000, 1760, and 1040 cm$^{-1}$; pmr (CDCl$_3$) δ7.4 (bs, 1H), 4.1 (q, 2H), 1.6 (bq, 2H), 1.3 (s, 3H) and 1.0 (t, 3H) ppm.

Anal. Calcd. for C$_6$H$_{11}$NO$_2$: C,55.79; H,8.59; N,10.85. Found: C,55.23; H,8.58; N,10.68.

PREPARATION 2

A mixture of 22.25 g. (0.25 mole) of 2-aminomethyl-2-propanol and 30.0 g. (0.5 mole) of urea were heated together at 170°–180°C. for 20 minutes, and the temperature was then increased to 200°–210°C. for an additional 20 minutes. On cooling, the brown solid was dissolved in water, the aqueous layer extracted with dichloromethane and the extracts combined and dried over anhydrous sodium sulfate. Following filtration, the dichloromethane was removed under reduced pressure to afford 13.1 g. (0.11 mole, 44%) of 5,5-dimethyl-2-oxazolidinone, m.p. 74°–77°C.; ir-3290 (N—H) and 1755 (C=O) cm$^{-1}$; pmr (CDCl$_3$) δ1.50 (s, 6H), 3.37 (s, 2H) and 6.77 (bs, 1H) ppm. [Lit. m.p. 79°–82°C., Close, J. Am. Chem. Soc. 73, 95 (1951)].

PREPARATION OF THE 3-CHLORO-2-OXAZOLIDINONES OF FORMULA I

EXAMPLE 1

A. Chlorine was bubbled through a solution of 8.7 g. (0.10 mole) of 2-oxazolidinone in 30 ml. of water at 0°C. for 30 minutes. A white solid precipitated, and the mixture was extracted with dichloromethane. The extracts were combined and dried over anhydrous sodium sulfate. Following filtration, the dichloromethane was removed under reduced pressure to afford a white solid, m.p. 58.5°–60°C. Sublimation of this material at 40°C./0.2 mm. gave 8.57 g. (0.071 mole, 71%) of 3-chloro-2-oxazolidinone (Walles Cpd. 3), m.p. 59°–61°C.; uv (H$_2$O) λ max 248 nm, ε=296 M$^{-1}$ cm$^{-1}$; pmr (CDCl$_3$) δ3.6–5.0 (AA'BB', 4H) ppm.

Anal. Calcd. for C$_3$H$_4$ClNO$_2$: C,29.65; H,3.32; N,11.53; Cl,29.2. Found: C,29.95; H,3.65; N,11.77; Cl,28.7.

Following a procedure similar to that described in Example 1, part (A) above, the following compounds of formula I were similarly prepared:

B. 3-Chloro-4-methyl-2-oxazolidinone, b.p. 85°–90°C./1 mm.; ir-3000, 1780, 1390, 1195 and 1040 cm$^{-1}$; pmr (CDCl$_3$) δ4.5 (m, 1H), 4.0 (m, 2H) and 1.4 (d, 3H, J=6Hz) ppm.

Anal. Calcd. for C$_4$H$_6$ClNO$_2$: C,35.44; H,4.46; N,10.33; Cl,26.2. Found: C,35.64; H,4.59; N,10.14; Cl,26.5.

C. 3-Chloro-4,5-dimethyl-2-oxazolidinone (Walles Cpd. 5), b.p. 60°–65°C./0.2 mm.; ir-3000, 1795, 1470, 1400, 1380, 1320 and 1215 cm$^{-1}$; pmr (CDCl$_3$) δ3.2–5.1 (m, 2H) and 1.4 (q with fine structure, 6H) ppm.

Anal. Calcd. for C$_5$H$_8$ClNO$_2$: C,40.15; H,5.39; N,9.37; Cl,23.7. Found: C,40,37; H,5.35; N,8.75; Cl,21.8.

D. 3-Chloro-5-methyl-2-oxazolidinone (Walles Cpd. 1), b.p. 70°–73°C./0.2 mm.; ir-1765 cm$^{-1}$; pmr (CDCl$_3$) δ4.80 (m, 1H), 4.2–3.2 (m, 2H) and 1.50 (d, 3H) ppm.

Anal. Calcd. for C$_4$H$_6$ClNO$_2$: C, 35.44; H,4.46; N,10.33; Cl,26.2. Found: C,35.90; H,5.03; N,9.71; Cl,25.0.

E. 3-Chloro-5-ethyl-2-oxazolidinone (Walles Cpd. 2), b.p. 88°–90°C./0.3 mm.; ir-1780 cm$^{-1}$; pmr (CDCl$_3$) δ4.60 (m, 1H), 4.2–3.2 (m, 2H), 1.77 (m, 2H) and 1.05 (t, 3H) ppm.

Anal. Calcd. for C$_5$H$_8$ClNO$_2$: C,40.15; H,5.39; N,9.37; Cl,23.7. Found: C,40.36; H,5.45; N,9.25; Cl,23.8.

F. 3-Chloro-4,4-dimethyl-2-oxazolidinone, m.p. 71°–72.5°C., sublimes at 60°C./0.25 mm., uv (H$_2$O) λmax 248 nm, ε=274 M$^{-1}$ cm$^{-1}$; pmr (CDCl$_3$) δ4.23 (s, 2H) and 1.40 (s, 6H) ppm.

Anal. Calcd. for C$_5$H$_8$ClNO$_2$: C,40.15; H,5.39; N,9.37; Cl,23.7. Found: C,40.36; H,5.36; N,9.35; Cl,23.4.

G. 3-Chloro-5,5-dimethyl-2-oxazolidinone, m.p. 58°–60°C., sublimes at 50°C./0.5 mm.; ir (NaCl) 3000, 2900, 1770, 1290 and 1125 cm$^{-1}$; pmr (CDCl$_3$) δ3.6 (s, 2H) and 1.6 (s, 6H) ppm.

Anal. Calcd. for C$_5$H$_8$ClNO$_2$: C,40.15; H,5.39; N,9.37; Cl,23.7. Found: C,40.39; H,5.36; N,9.42; Cl,22.6.

H. 3-Chloro-4-ethyl-4-methyl-2-oxazolidinone, ir-3000, 1780 and 1075 cm$^{-1}$; pmr (CDCl$_3$) δ4.3 (t, 2H), 1.8 (bq, 2H), 1.4 (s, 3H) and 0.98 (t, 3H) ppm.

Anal. Calcd. for C$_6$H$_{10}$ClNO$_2$: C,44.04; H,6.12; N,8.57; Cl,21.7. Found: C,44.23; H,6.30; N,8.29 Cl,21.2.

EXAMPLE 2

To a suspension of 4.0 g. (0.35 mole) of trichloroisocyanuric acid in 20 ml. of dichloromethane was added 4.0 g. (0.035 mole) of 4,5-dimethyl-2-oxazolidinone. The mixture was stirred for 2 hours, a white solid which separated was removed by filtration, and the filtrate taken to dryness under reduced pressure. Distillation of the residue gave 3.4 g. (0.023 mole, 66%) of 3-chloro-4,5-dimethyl-2-oxazolidinone, b.p. 85°–90°C./0.5 mm., identical with that obtained by the procedure described in Example 1, part (C) above as shown by infrared and proton magnetic resonance spectra of the two samples.

The compounds of the invention and certain reference compounds were tested in the germicidal efficiency test, a modification of the standard serial dilution test, against *Staphylococcus aureus* ATCC 6538. In the germicidal efficiency test, instead of determining the minimum inhibitory concentration as in the serial dilution test procedure, the time required to effect complete sterilization of the micro-organism when exposed to a given concentration of the test substance is determined. This procedure affords a basic of comparison of the time dependent efficacies of the various test substances which gives a measure not only of the germicidal efficacy of the test species but, since as will be seen germicidal efficiency of the N-chloro compounds generally tends to diminish with time, apparently owing to decomposition of, and therefore dilution of, the active species, the test procedure also provides an indication of the efficacy to be expected at varying time intervals after solution of the test species in the application medium. The test procedure is described as follows: A stock solution of known concentration of each compound to be tested was prepared in 0.1M sodium dihydrogen phosphate buffered to pH 7.0. To 5 ml. of the test solution was added 0.2 ml. of an overnight broth culture containing from 6×10$^6$ to 8×10$^6$ organisms/ml. of *Staphylococcus aureus* ATCC 6538 and 5 g. of gelysate peptone and 3 g. of beef extract per 1000 ml. of water. At time intervals of 0.5, 1, 2, 3, 4, 5, 6, 7, 8, 9, 10, 15 and 30 minutes, a loop of this suspension was subcultured into 5 ml. of sterile nutrient broth (5 g. of gelysate peptone and 3 g. of beef extract/1000 ml. of water), and the samples were incubated at 37°C. for 7 days with daily observation for evidence of bacterial growth. The time interval in which no bacterial growth was observed after the incubation period in a particular sample was recorded as the end point.

The germicidal kill times so-obtained at various concentrations of the compounds of the invention and of certain reference compounds are given in Table A below. The compounds are identified in each case by the Example number above where the compounds are described. Here and elsewhere in the specification that follows, concentrations are expressed in parts per million (ppm) of "positive" chlorine, which was determined in each instance by addition of excess aqueous potassium iodide to an acidified solution of the test compound and titration of the iodine liberated with standard sodium thiosulfate solution.

Table A

| Compound/Example No. | Concentration ppm + Cl | Bactericidal Time (Minutes) |
|---|---|---|
| 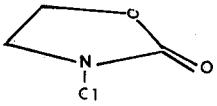<br>1A (Walles Cpd. 3) | 465<br>281<br>157<br>70 | 1<br>2<br>7<br>10<t≤15 |
| 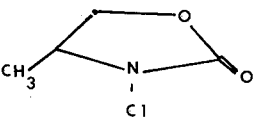<br>1B | 610<br>303<br>131 | 1<br>4<br>7 |
| 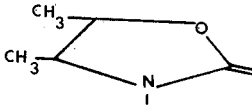<br>1C (Walles Cpd. 5) | 490<br>295<br>173<br>117 | 4<br>5<br>10<t≤15<br>10 |
| 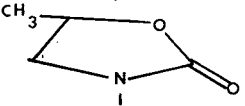<br>1D (Walles Cpd. 1) | 548<br>383<br>190<br>74 | 0.5<br>2<br>15<t≤30<br>>30 |
| 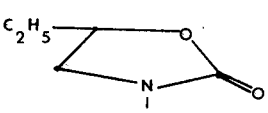<br>1E (Walles Cpd. 2) | 535<br>372<br>161<br>96 | 1<br>3<br>2<br>6 |
| 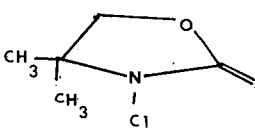<br>1F | 508<br>368<br>195<br>148 | 2<br>3<br>5<br>5 |
| 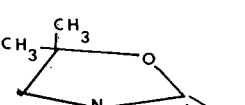<br>1G | 473<br>104 | 7<br>15<t≤30 |

The stabilities and the time-dependent efficacies of the claimed and reference species were determined by comparing the contact germicidal times and the initial and final concentrations of positive chlorine in solutions of the test species in 0.1M sodium dihydrogen phosphate buffered to pH 7.0 before and after 14 day incubation of the solutions at 40°C. The results are given in Table B below, where the columns headed "$B_c$ Time" refers to the bactericidal time in minutes.

Table B

| Example No. | Initial Concn. ppm + Cl | $B_c$ Time | Final Conc. ppm + Cl | $B_c$ Time |
|---|---|---|---|---|
| 1A (Walles Cpd. 3) | 465 | 1 | 30 | >30 |
| 1B | 610 | 1 | 14 | >30 |
| 1C (Walles Cpd. 5) | 490 | 4 | 51 | $15 < t \leq 30$ |
| 1D (Walles Cpd. 1) | 548 | 0.5 | 34 | >30 |
| 1E (Walles Cpd. 2) | 535 | 1 | 15 | >30 |
| 1F | 534 | 2 | 527 | 2 |
| 1G | 473 | 7 | 43 | $10 < t \leq 15$ |
| 1H | 555 | 3 | 553 | 3 |

These results show that, with the exception of the compound of Example 1C (Walles Cpd. 5), each of the reference compounds decomposed over the test period to the point where each had lost measurable bactericidal activity. On the other hand, 3-chloro-4,4-dimethyl-2-oxazolidinone and 3-chloro-4-ethyl-4-methyl-2-oxazolidinone, the compounds of Examples 1F and 1H, respectively, had decomposed only slightly over the test period and had retained the original level of bactericidal activity, while 3-chloro-5,5-dimethyl-2-oxazolidinone, the compound of Example 1G, although substantially decomposed over the test period, nevertheless retained a good measure of bactericidal activity superior to each of the reference species, including that of Example 1C.

A further measure of the relative stabilities of the reference and claimed species was obtained by measuring the hydrolytic stability of the various species in 0.1M sodium dihydrogen phosphate buffered to pH 7.0 at 40°. For each species, the rate of change in the concentration of positive chlorine in the solution was measured by the volume of standard thiosulfate required to titrate a series of aliquots of a standard volume of the solution at various time intervals using potassium iodide/sodium thiosulfate as detailed above. The volumes of thiosulfate required to titrate each sample so obtained were interpreted as first-order kinetic processes. The hydrolytic stabilities of the reference and claimed species under the experimental conditions were characterized by the reaction rate constants and half-lives obtained from a linear regression analysis of the experimental data. The results obtained are given in Table C below and are also shown in FIG. 1 where the volumes in milliliters of standard thiosulfate required to titrate the positive chlorine in the various samples are plotted as ordinate against time in days as abscissa.

Table C

| Example No. | Half-Life (Hours) | Rate Constant $k \times 10^{-2}$ (hr$^{-1}$) | Correlation Coefficient |
|---|---|---|---|
| 1A (Walles Cpd. 3) | 45 | 1.55 | 0.9995 |
| 1B | 10.9 | 6.33 | 0.9825 |
| 1C (Walles Cpd. 5) | 38.5 | 1.80 | 0.9929 |
| 1F | 2038 | 0.034 | 0.9899 |
| 1G | 86.6 | 0.80 | 0.9763 |

These results again demonstrate the unusual stability of 3-chloro-4,4-dimethyl-2-oxazolidinone, the compound of Example 1F. They also show that, although the isomeric 3-chloro-5,5-dimethyl-2-oxazolidinone of Example 1G is somewhat less stable than the corresponding 4,4-dimethyl compound, surprisingly the half-life of the former is from around twice to eight times as great as the half-lives of the reference species studied.

As a final measure of the relative stabilities of the claimed and reference species, the stabilities of the 3-chloro-2-oxazolidinones in the neat state (i.e., the pure materials containing no added diluent or adulterant) were determined at 40°C. except in those cases where the compound proved to be so unstable that no significant data could be accumulated. In those instances, the data were acquired at ambient temperature (approximately 23°C.). The method used was similar to that described above in which the rate of disappearance of positive chlorine was followed iodometrically by titration of iodine liberated from added potassium iodide with standard sodium thiosulfate solution. Samples of the compounds were individually sealed in ampoules and stored in the dark at 23°C. or 40°C. and weighed amounts removed from time to time for analysis. The results obtained are given in Table D below.

Table D

| Compound - Example 1A (Walles Cpd. 3) (T=40°C.) | | Compound - Example 1B (T=23°C.) | |
|---|---|---|---|
| Time (Hrs.) | % Cl | Time (Hrs.) | % Cl |
| 0 | 28.9 | 0 | 26.5 |
| 2 | 27.4 | 3 | 25.9 |
| 18.5 | 25.9 | 5 | 25.3 |
| 24 | 26.9 | 6.5 | 25.0 |
| 54 | 27.2 | 9 | 25.0 |
| 72 | 24.8 | 10.5 | 24.1 |
| 80 | 23.5 | 21.5 | 21.7 |
| 98 | 26.2 | 24.5 | 21.1 |
| 144 | 8.7 | 29 | 14.4 |
| 168 | 0.4 | 30 | 12.4 |
| | | 32 | 6.1 |
| | | 35 | 2.0 |
| | | 45 | 0 |

| Compound - Example 1C (Walles Cpd. 5) (T=23°C.) | | Compound - Example 1F (T=40°C.) | |
|---|---|---|---|
| Time (Hrs.) | % Cl | Time (Days) | % Cl |
| 0 | 21.8 | 0 | 23.4 |
| 3 | 20.8 | 1 | 23.0 |
| 5 | 8.2 | 2 | 23.8 |
| 7.5 | 0.47 | 7 | 23.5 |
| 24 | 0.17 | 35 | 24.2 |
| | | 49 | 23.3 |

| Compound - Example 1G (T=40°C.) | | Compound - Example 1H (T=40°C.) | |
|---|---|---|---|
| Time (Days) | % Cl | Time (Days) | % Cl |
| 0 | 19.6 | 0 | 21.7 |
| 1 | 22.1 | 2 | 23.6 |
| 4 | 23.7 | 5 | 21.1 |
| 7 | 16.5 | 10 | 20.7 |
| 11 | 18.1 | 14 | 21.0 |
| 15 | 14.4 | 18 | 20.6 |
| 19 | 10.0 | 25 | 18.2 |
| 22 | 0 | 39 | 22.3 |
| | | 53 | 20.2 |
| | | 164 | 19.6 |

For each of the compounds analyzed as indicated above, percent chlorine was plotted as ordinate against time in days as abscissa on semi-logarithmic paper and the points connected by a smooth curve for each compound. Inspection of plots somade, which are shown in FIG. 2, again shows the surprising stability of 3-chloro-4,4-dimethyl-2-oxazolidinone (Example 1F), 3-chloro-4-ethyl-4-methyl-2-oxazolidinòne (Example 1H) and 3-chloro-5,5-dimethyl-2-oxazolidinone (Example 1G) as compared with the various reference species.

We claim:

1. A compound having the formula:

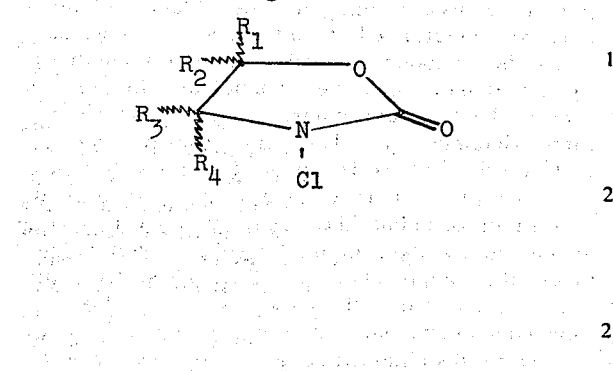

where either $R_1$ and $R_2$ are the same or different non-tertiary lower-alkyl, and $R_3$ and $R_4$ are each hydrogen or $R_1$ and $R_2$ are each hydrogen, and $R_3$ and $R_4$ are the same or different non-tertiary lower-alkyl.

2. A compound according to claim 1 where $R_1$ and $R_2$ are each hydrogen, and $R_3$ and $R_4$ are the same or different lower-alkyl.

3. A compound according to claim 1 where $R_3$ and $R_4$ are each hydrogen, and $R_1$ and $R_2$ are the same or different lower-alkyl.

4. A compound according to claim 2 where $R_3$ and $R_4$ are the same lower-alkyl.

5. 3-Chloro-4,4-dimethyl-2-oxazolidinone according to claim 4.

6. 3-Chloro-4-ethyl-4-methyl-2-oxazolidinone according to claim 2.

7. 3-Chloro-5,5-dimethyl-2-oxazolidinone according to claim 3.

* * * * *